United States Patent
Tanaka et al.

(10) Patent No.: US 12,138,584 B2
(45) Date of Patent: Nov. 12, 2024

(54) COMPOSITE AMINE ABSORBENT, REMOVAL UNIT, AND REMOVAL METHOD

(71) Applicants: MITSUBISHI HEAVY INDUSTRIES, LTD., Tokyo (JP); The Kansai Electric Power Co., Inc., Osaka (JP)

(72) Inventors: Hiroshi Tanaka, Tokyo (JP); Takashi Kamijo, Tokyo (JP); Takuya Hirata, Tokyo (JP); Tatsuya Tsujiuchi, Tokyo (JP); Takuya Sugiura, Toyko (JP)

(73) Assignees: MITSUBISHI HEAVY INDUSTRIES, LTD., Tokyo (JP); The Kansai Electric Power Co., Inc., Osaka (JP)

( * ) Notice: Subject to any disclaimer, the term of this patent is extended or adjusted under 35 U.S.C. 154(b) by 0 days.

(21) Appl. No.: 18/282,154

(22) PCT Filed: Apr. 28, 2022

(86) PCT No.: PCT/JP2022/019243
§ 371 (c)(1),
(2) Date: Sep. 14, 2023

(87) PCT Pub. No.: WO2023/209931
PCT Pub. Date: Nov. 2, 2023

(65) Prior Publication Data
US 2024/0042377 A1 Feb. 8, 2024

(51) Int. Cl.
*B01D 53/14* (2006.01)
*B01D 53/18* (2006.01)
(Continued)

(52) U.S. Cl.
CPC ..... *B01D 53/1493* (2013.01); *B01D 53/1425* (2013.01); *B01D 53/1462* (2013.01);
(Continued)

(58) Field of Classification Search
None
See application file for complete search history.

(56) References Cited

U.S. PATENT DOCUMENTS 5,597,678 A * 1/1997 Honda .................... G03F 7/422
430/258
9,155,998 B2 10/2015 Saiwan et al.
(Continued)

FOREIGN PATENT DOCUMENTS

CN 109420409 A 3/2019
JP 2007-527791 A 10/2007
(Continued)

OTHER PUBLICATIONS

Office Action issued in counterpart Japanese Patent Application No. JP 2022-574834 A, dated Feb. 21, 2023 (6 pages).
(Continued)

*Primary Examiner* — Daniel Berns
(74) *Attorney, Agent, or Firm* — Osha Bergman Watanabe & Burton LLP (57) ABSTRACT

A composite amine absorbent to absorb at least one of $CO_2$ and $H_2S$ in a gas includes: a chain monoamine; a diamine; a cyclic compound represented by the following chemical formula:

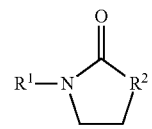

where $R^1$: any one of hydrogen, a hydrocarbon group having a carbon number of 1 to 4, and a hydroxyalkyl group, $R^2$: oxygen or $N-R^3$, and $R^3$: any one of hydrogen, a hydro-
(Continued)

carbon group having a carbon number of 1 to 4, and a hydroxyalkyl group; and water.

13 Claims, 4 Drawing Sheets

(51) Int. Cl.
   *B01D 53/52* (2006.01)
   *B01D 53/62* (2006.01)
   *B01D 53/78* (2006.01)
   *B01D 53/96* (2006.01)

(52) U.S. Cl.
   CPC ..... *B01D 53/1468* (2013.01); *B01D 53/1475* (2013.01); *B01D 53/18* (2013.01); *B01D 53/526* (2013.01); *B01D 53/62* (2013.01); *B01D 53/78* (2013.01); *B01D 53/96* (2013.01); *B01D 2252/20405* (2013.01); *B01D 2252/2041* (2013.01); *B01D 2252/20447* (2013.01); *B01D 2252/20484* (2013.01); *B01D 2252/504* (2013.01); *B01D 2257/304* (2013.01); *B01D 2257/504* (2013.01)

(56) References Cited

U.S. PATENT DOCUMENTS

| | | |
|---|---|---|
| 10,960,346 B2 | 3/2021 | Tanaka et al. |
| 11,135,544 B2 | 10/2021 | Suzuki et al. |
| 2008/0098892 A1 | 5/2008 | Asprion et al. |
| 2015/0125372 A1 | 5/2015 | Stites et al. |
| 2017/0001142 A1 | 1/2017 | Rayner et al. |
| 2017/0282116 A1 | 10/2017 | Ingram et al. |
| 2019/0126194 A1 | 5/2019 | Ingram et al. |
| 2019/0151794 A1 | 5/2019 | Tanaka et al. |
| 2020/0291901 A1* | 9/2020 | Song ............... F02M 21/0215 |

FOREIGN PATENT DOCUMENTS

| | | |
|---|---|---|
| JP | 2017-507771 A | 3/2017 |
| JP | 2017-104775 A | 6/2017 |
| JP | 2017-537437 A | 12/2017 |
| JP | 2018-122278 A | 8/2018 |
| JP | 2018-183729 A | 11/2018 |
| JP | 2019-520201 A | 7/2019 |
| JP | 2020-022933 A | 2/2020 |
| JP | 2020-044489 A | 3/2020 |
| JP | 6841676 B2 | 3/2021 |

OTHER PUBLICATIONS

Written Opinion and International Search Report issued in corresponding International Application No. PCT/JP2022/019243, dated Jul. 19, 2022 (12 pages).
The First Office Action issued in counterpart Chinese Patent Application No. 202280021302.X, dated Jan. 26, 2024 (18 pages).

* cited by examiner

COMPOSITE AMINE ABSORBENT, REMOVAL UNIT, AND REMOVAL METHOD

FIELD

The present disclosure relates to a composite amine absorbent, a removal unit, and a removal method.

BACKGROUND

In recent years, a greenhouse effect caused by $CO_2$ has been pointed out as one of the causes of a global warming phenomenon and thus countermeasures of the global warming phenomenon have become an urgent task in protecting the global environment. Generation sources of $CO_2$ include every field of human activity in which fossil fuels are burnt and requirements for reduction in the exhaust of $CO_2$ tend to increase more and more. With this tendency, methods for bringing flue gas of boilers into contact with an amine-based $CO_2$ absorbent to remove and recover $CO_2$ in flue gases and methods for storing the recovered $CO_2$ without releasing the recovered $CO_2$ into the atmosphere have been intensively studied for power generation facilities using a large quantity of fossil fuels such as thermal power stations. As a process for removing and recovering $CO_2$ in the flue gas using the amine-based $CO_2$ absorbent, a process for bringing the flue gas into contact with the $CO_2$ absorbent in an absorber, heating the absorbent in which $CO_2$ is absorbed in a regenerator, and releasing $CO_2$ and reusing the absorbent by regenerating the absorbent and circulating the regenerated absorbent in the absorber has been employed.

As the $CO_2$ absorbent, for example, an absorbent including amine compounds has been developed (refer to Patent Literature 1 to Patent Literature 5).

CITATION LIST

Patent Literature

Patent Literature 1: Japanese Patent Application Laid-open No. 2018-183729
Patent Literature 2: Japanese Patent Application Laid-open No. 2020-022933
Patent Literature 3: Japanese Patent Application Laid-open No. 2020-044489
Patent Literature 4: Published Japanese Translation of PCT International Publication for Patent Application No. 2007-527791
Patent Literature 5: Japanese Patent Application Laid-open No. 2018-122278
Patent Literature 6: Japanese Patent No. 6841676

SUMMARY

Technical Problem

Use of the absorbents described in Patent Literature 1 to Patent Literature 5 allows at least one of $CO_2$ and $H_2S$ included in a processing-target gas to be separated from the gas by the absorbent. Here, as the absorbing performance of the absorbent becomes better, the absorbent can more efficiently recover $CO_2$ and $H_2S$ that are target to be absorbed. Here, an absorbent having a low performance of releasing absorbed $CO_2$ and $H_2S$ results in requiring more energy for releasing $CO_2$ and $H_2S$ from the absorbent, and thus an increase in efficiency as the unit is limited.

With the view of the above problem, an object of the present disclosure is to provide a composite amine absorbent, a removal unit, and a removal method in which an absorbing performance is excellent and absorbed $CO_2$ and $H_2S$ can be efficiently released.

Solution to Problem

To solve the above problem, a composite amine absorbent according to the present disclosure absorbs at least one of $CO_2$ and $H_2S$ in a gas. The composite amine absorbent includes:
  a chain monoamine (a);
  a diamine (b);
  a cyclic compound (c) represented by following chemical formula:

where $R^1$: any one of hydrogen, a hydrocarbon group having a carbon number of 1 to 4, and a hydroxyalkyl group,
  $R^2$: oxygen or N—$R^3$, and
  $R^3$: any one of hydrogen, a hydrocarbon group having a carbon number of 1 to 4, and a hydroxyalkyl group; and
  water (d).

To solve the above problem, a removal unit according to the present disclosure uses the above described composite amine absorbent. The removal unit includes: an absorber configured to bring a gas including at least one of $CO_2$ and $H_2S$ into contact with the absorbent to remove at least one of $CO_2$ and $H_2S$; and an absorbent regenerator configured to regenerate a solution absorbing at least one of $CO_2$ and $H_2S$. The regenerated solution formed by removing at least one of $CO_2$ and $H_2S$ in the absorbent regenerator is reused in the absorber.

To solve the above problem, a removal method according to the present disclosure uses the above-described composite amine absorbent. The removal method includes: bringing a gas including at least one of $CO_2$ and $H_2S$ into contact with the absorbent to remove at least one of $CO_2$ and $H_2S$ in an absorber; regenerating a solution absorbing at least one of $CO_2$ and $H_2S$ in an absorber regenerator; and reusing in the absorber the solution regenerated by removing at least one of $CO_2$ and $H_2S$ in the absorbent regenerator.

Advantageous Effects of Invention

According to the present disclosure, a linear chain monoamine (a), a diamine (b), and a cyclic compound (c) satisfying the chemical formula are dissolved in water to form an absorbent, whereby absorbed $CO_2$ and $H_2S$ can be efficiently released and energy efficiency can be improved, while the absorbent maintains absorbing properties of $CO_2$ or $H_2S$ or both due to interaction in a composite manner and the synergistic effect of these compounds.

DESCRIPTION OF EMBODIMENTS

Hereinafter, suitable Examples of the present disclosure will be described in detail with reference to the attached drawings. The present disclosure, however, is not limited by these Examples. In the case where a plurality of Examples exist, the present disclosure also includes configurations in which Examples each are combined.

The composite amine absorbent according to the present disclosure is an absorbent to absorb at least one of $CO_2$ and $H_2S$ and comprises a chain monoamine (a), a diamine (b), and a cyclic compound (c) represented by the chemical formula illustrated in "Chemical Formula 2", and water (d).

$R^1$: any one of hydrogen, a hydrocarbon group having a carbon number of 1 to 4, and a hydroxyalkyl group
$R^2$: oxygen or N—$R^3$
$R^3$: any one of a hydrogen, a hydrocarbon group having a carbon number of 1 to 4, and a hydroxyalkyl group In other words, the composite amine absorbent is a liquid in which the chain monoamine (a), the diamine (b), and the cyclic compound (c) represented by the above chemical formula are dissolved in water. In the present disclosure, the chain monoamine (a), the diamine (b), and the cyclic compound (c) represented by the above chemical formula are dissolved in water to form the absorbent, whereby the absorbed gas stripping properties are excellent, while the absorbent maintains the absorbing properties of $CO_2$ or $H_2S$ or both to a gas including at least one of $CO_2$ and $H_2S$ due to interaction in a composite manner and the synergistic effect of these compounds. In other words, the heat duty required for release at a reboiler can be reduced while the reaction rate of the absorbent is kept high.

Here, the linear chain monoamine (a) (Component a) includes at least one of a primary linear chain monoamine (Component a1, a primary chain monoalkanolamine), a secondary linear chain monoamine (Component a2, a secondary chain monoalkanolamine), and a tertiary linear chain monoamine (Component a3, a tertiary chain monoalkanolamine). A combination of the two-component linear chain amines of the primary linear chain monoamine and the secondary linear chain monoamine, a combination of the two-component linear chain amines of the primary linear chain monoamine and the tertiary linear chain monoamine, a combination of the two-component linear chain amines of the primary linear chain monoamine and the tertiary linear chain monoamine, and a combination of the three-component linear chain amines of the primary linear chain monoamine, the secondary linear chain monoamine, and the tertiary linear chain monoamine may also be employed.

As the primary linear chain monoamine (Component a1, a primary chain monoalkanolamine), a primary monoamine having a low steric hindrance property (Component a1L) or a primary monoamine having a high steric hindrance property (Component a1H) is preferable. Here, in the primary linear chain monoamine, examples of the primary monoamine having the low steric hindrance property (Component a1L) include at least one compound selected from monoethanolamine (MEA), 3-amino-1-propanol, 4-amino-1-butanol, and diglycol amine. A combination of these amines may also be employed.

In the primary linear chain monoamine, compounds represented by the chemical formula illustrated in "Chemical Formula 3" are preferable as the primary monoamine having the high steric hindrance property (Component a1H).

(1)

$R_{11}$ TO $R_{13}$: HYDROGEN OR HYDROCARBON GROUP HAVING CARBON NUMBER OF 1 TO 3

Specific examples of the primary monoamine having the high steric hindrance property (Component a1H) include at least one compound selected from 2-amino-1-propanol (2A1P), 2-amino-1-butanol (2A1B), 2-amino-3-methyl-1-butanol (AMB), 1-amino-2-propanol (1A2P), 1-amino-2-butanol (1A2B), and 2-amino-2-methyl-1-propanol (AMP). The present disclosure, however, is not limited to these compounds. A combination of these amines may also be employed.

As the secondary linear chain monoamine (a2), compounds represented by the chemical formula illustrated in "Chemical Formula 4" are preferable.

(2)

$R_{14}$: STRAIGHT CHAIN HYDROCARBON GROUP HAVING CARBON NUMBER OF 1 TO 4
$R_{15}$: HYDROXY ALKYL GROUP HAVING CARBON NUMBER OF 1 TO 4

Specific examples of the secondary linear chain monoamine (a2, a secondary chain monoalkanolamine) include at least one compound selected from N-methylaminoethanol, N-ethylaminoethanol, N-propylaminoethanol, and N-butylaminoethanol. The present disclosure, however, is not limited to these compounds. A combination of these amines may also be employed.

As the tertiary linear chain monoamine (a3), compounds represented by the chemical formula illustrated in "Chemical Formula 5" are preferable.

(3)

$R_{16}$: HYDROCARBON GROUP HAVING CARBON NUMBER OF 1 TO 4
$R_{17}$: HYDROCARBON GROUP OR HYDROXY ALKYL GROUP HAVING CARBON NUMBER OF 1 TO 4
$R_{18}$: HYDROCARBON GROUP OR HYDROXY ALKYL GROUP HAVING CARBON NUMBER OF 1 TO 4

Specific examples of the tertiary linear chain monoamine (a3, a tertiary chain monoalkanolamine) include at least one compound selected from N-methyldiethanolamine, N-ethyldiethanolamine, N-butyldiethanolamine, 4-dimethylamino-1-butanol, 2-dimethylaminoethanol, 2-diethylaminoethanol, 2-di-n-butylaminoethanol, N-ethyl-N-methylethanolamine, 3-dimethylamino-1-propanol, and 2-dimethylamino-2-methyl-1-propanol. The present disclosure, however, is not limited to these compounds. A combination of these amines may also be employed.

The diamine (b) (Component b) includes at least one diamine containing amino groups having the same number of substituents. The diamine containing the amino groups having the same number of substituents preferably includes at least one of a primary linear chain polyamine, a secondary linear chain polyamine, and a secondary cyclic polyamine.

Here, examples of the primary linear chain polyamine include at least one compound selected from ethylenediamine (EDA) and propanediamine (PDA). The present disclosure, however, is not limited to these compounds. Examples of the secondary linear chain polyamine include at least one compound selected from N,N'-dimethylethylenediamine (DMEDA), N,N'-diethylethylenediamine (DEEDA), and N,N'-dimethylpropanediamine (DMPDA). The present disclosure, however, is not limited to these compounds. A combination of these amines may also be employed.

Examples of the secondary cyclic polyamine include at least one compound selected from piperazine (PZ), 2-methylpiperazine (2MPZ), and 2,5-dimethylpiperazine (DMPZ). The present disclosure, however, is not limited to these compounds. A combination of these amines may also be employed.

The diamine (Component b) includes at least one diamine containing amino groups having the same number of substituents (b1) and at least one linear diamine containing amino groups having different numbers of substituents (b2). As the diamine containing amino groups having the same number of substituents (b1), the various amines described above may be used.

The linear diamine containing amino groups having the different numbers of substituents (b2) satisfies the chemical formula illustrated in [Chemical Formula 6].

$R^4$: any one of a hydrogen, a hydrocarbon group having a carbon number of 1 to 4, and a hydroxyalkyl group
$R^5$: any one of a hydrogen, a hydrocarbon group having a carbon number of 1 to 4, and a hydroxyalkyl group
$R^6$: a hydroxy alkyl group
In the case where $R^4$ is not hydrogen, $R^5$ is also not hydrogen As the cyclic compound (Component c), various compounds satisfying the following chemical formula may be used as described above.

$R^1$: any one of hydrogen, a hydrocarbon group having a carbon number of 1 to 4, and a hydroxyalkyl group
$R^2$: oxygen or N—$R^3$
$R^3$: any one of a hydrogen, a hydrocarbon group having a carbon number of 1 to 4, and a hydroxyalkyl group Here, the cyclic compound is preferably a cyclic compound in which $R^1$ in [Chemical Formula 7] is hydrogen or the hydrocarbon group same as $R^{14}$ and $R^{16}$ to $R^{18}$, and $R^2$ is oxygen or $R^3$ is the hydrocarbon group same as $R^{14}$ and $R^{16}$ to $R^{18}$.

Subsequently, the blending ratios of each of the components (Component a, Component b, and Component c) are preferably determined as follows. The total concentration of the linear chain monoamine (a) (Component a), the diamine (b) (Component b), and the cyclic compound (c) satisfying the chemical formula is preferably 20% by weight or more and 80% by weight or less relative to the entire absorbent, more preferably 30% by weight or more and 75% by weight or less relative to the entire absorbent, and further preferably 40% by weight or more and 70% by weight or less relative to the entire absorbent. Setting the total concentration within this range allows the absorbent to excellently function.

The linear chain monoamine (a) (Component a) is preferably 15% by weight or more and 60% by weight or less relative to the entire absorbent and further suitably 20% by weight or more and 55% by weight or less relative to the entire absorbent. The diamine (b) (Component b) is preferably 1% by weight or more and 25% by weight or less relative to the entire absorbent and further suitably 2% by weight or more and 20% by weight or less relative to the entire absorbent. The cyclic compound (c) satisfying the chemical formula is preferably 1% by weight or more and 30% by weight or less relative to the entire absorbent and further suitably 1% by weight or more and 20% by weight or less relative to the entire absorbent.

As the blending ratio of the diamine (b) (Component b) and the cyclic compound (c) (Component c) satisfying the chemical formula to the linear chain monoamine (a) (Component a), a blend in a weight ratio of (diamine (b)+cyclic compound (c) satisfying the chemical formula)/(chain monoamine (a)) of 0.033 or more and 3.7 or less, that is, $0.033 \leq (b+c)/a \leq 3.7$ is preferable and a blend of $0.067 \leq (b+c)/a \leq 0.75$ is more preferable.

The blend ratio of the diamine (b) to the cyclic compound (c) satisfying the chemical formula is preferably a weight ratio of diamine (b)/cyclic compound (c) satisfying the chemical formula of 0.033 or more and 18 or less. In other words, a blend of $0.033 \leq b/c \leq 18$ is preferable and a blend of $0.20 \leq b/c \leq 5.0$ is more preferable.

As the blend ratio of water, the blend ratio (% by weight) of water (Component d) is determined to be the remainder of the total weight of the linear chain monoamine (a), the diamine (b), and the cyclic compound (c) satisfying the chemical formula.

In the present disclosure, the absorption temperature in the absorber of the chemical absorption method at the time of contact with the flue gas including, for example, $CO_2$ is preferably set to the range of 30° C. to 80° C. To the absorbent used in the present disclosure, a corrosion inhibitor, an antidegradation agent, and the like are added, if necessary.

As a partial pressure of $CO_2$ at the $CO_2$ absorber inlet at the time of absorption of $CO_2$ in the gas to be processed, a low $CO_2$ partial pressure (for example, 0.003 MPa to 0.1 MPa) is preferable from the view point of the application of the chemical absorption method.

In the present disclosure, as the regeneration temperature in the regenerator that releases $CO_2$ and the like from the absorbent in which $CO_2$ and the like are absorbed, the bottom temperature of the absorbent regenerator is preferably 110° C. or more in the case where the pressure in the regenerator is 130 kPa to 200 kPa (absolute pressure). This is because regeneration at a temperature of less than 110° C. requires a larger circulation volume of the absorbent in the system, which is not preferable from the viewpoint of regeneration efficiency. More suitably, regeneration at a temperature of 115° C. or more is preferable.

Examples of gases to be processed by the present disclosure include, but are not limited to, coal gasification gases, synthesis gases, coke oven gases, petroleum gases, natural gases, and flue gases. Any gases that include acidic gases such as $CO_2$ and $H_2S$ are acceptable.

The processes that can be employed in the method of the present disclosure for removing $CO_2$ or $H_2S$ or both from the gases are not limited. An example of a removal unit that removes $CO_2$ will be described with reference to FIG. 1.

Figure 1:
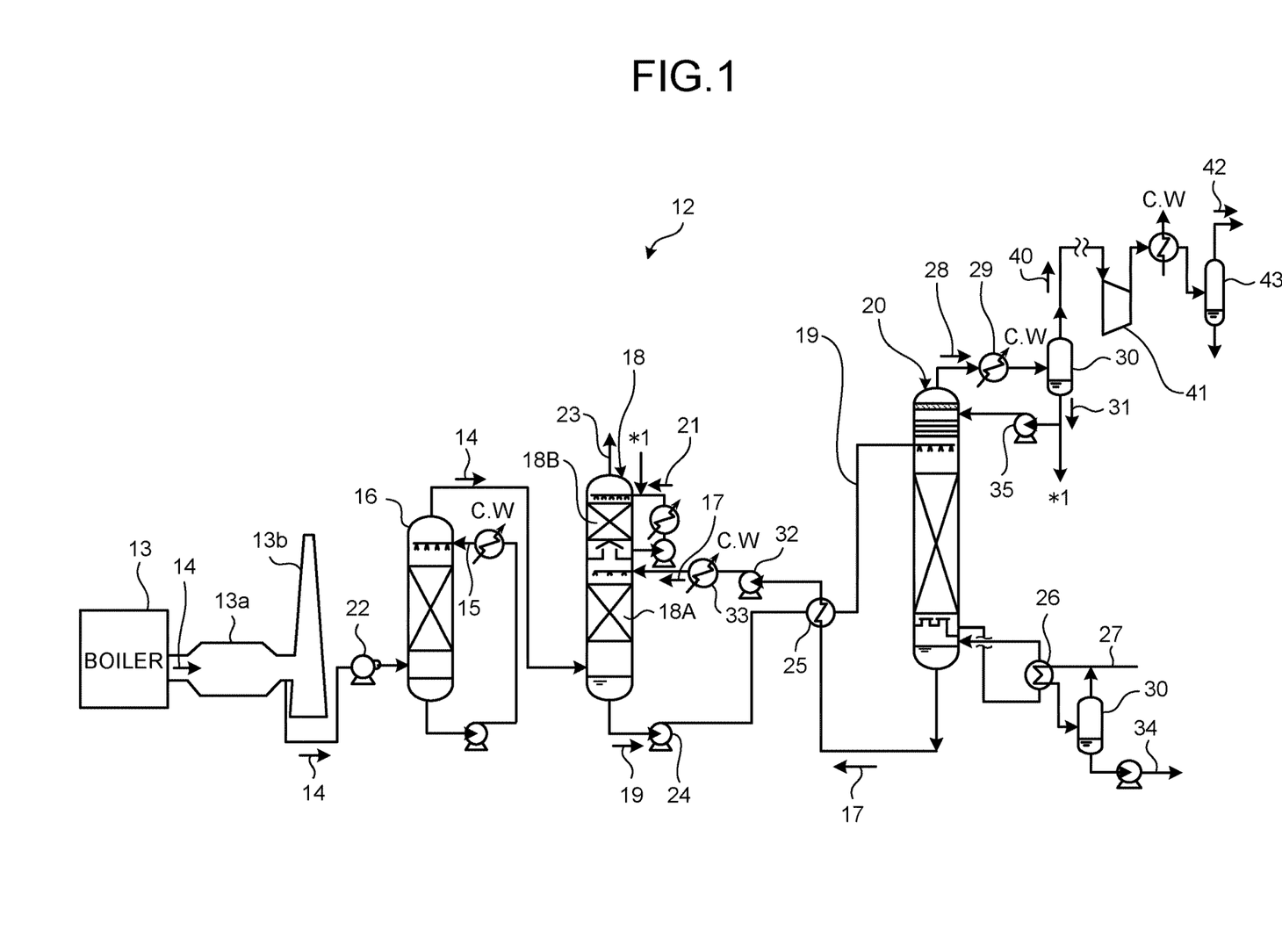
FIG. 1 is a schematic view illustrating the configuration of a $CO_2$ recovery unit apparatus using the absorbent of the present disclosure.

FIG. 1 is a schematic view illustrating the configuration of a $CO_2$ recovery unit according to Example 1. As illustrated in FIG. 1, a $CO_2$ recovery unit 12 according to Example 1 includes a flue gas cooling device 16 cooling a flue gas 14 including $CO_2$ and $O_2$ discharged from industrial combustion facilities 13 such as a boiler and a gas turbine with cooling water 15, a $CO_2$ absorber 18 including a $CO_2$ recovery section 18A removing $CO_2$ from the flue gas 14 by bringing the flue gas 14 including cooled $CO_2$ into contact with the $CO_2$ absorbent (hereinafter, also referred to as an "absorbent") 17 absorbing $CO_2$, and an absorbent regenerator 20 regenerating the $CO_2$ absorber by releasing $CO_2$ from the $CO_2$ absorber (hereinafter, also referred to as a "rich solution") 19 in which $CO_2$ is absorbed. In the $CO_2$ recovery unit 12, the regenerated $CO_2$ absorbent (hereinafter, also referred to as a "lean solution") 17 from which $CO_2$ is removed in the absorbent regenerator 20 is reused in the $CO_2$ absorber 18 as the $CO_2$ absorbent.

In FIG. 1, a symbol 13a is a flue gas duct, a symbol 13b is a stack, and a symbol 34 is condensed water of steam. The $CO_2$ recovery unit 12 may be installed afterward to recover $CO_2$ from an existing flue gas source or may be installed simultaneously for a new flue gas source. A damper that can be opened and closed is installed in the line for the flue gas 14 and is opened when the $CO_2$ recovery unit 12 is under operation. The flue gas source is set to close when the operation of the $CO_2$ recovery unit 12 is stopped, while the flue gas source is still operating.

In the $CO_2$ recovery method using this $CO_2$ recovery unit 12, the pressure of the flue gas 14 from the industrial combustion facilities 13 such as a boiler and a gas turbine including $CO_2$ is firstly raised by a flue gas blower 22. Thereafter, the flue gas is sent to a flue gas cooling device 16, cooled with cooling water 15 in this device, and sent to a $CO_2$ absorber 18.

In the $CO_2$ absorber 18, the flue gas 14 is in countercurrent contact with the $CO_2$ absorbent 17 serving as the amine absorbent according to this Example and $CO_2$ in the flue gas 14 is absorbed into the $CO_2$ absorbent 17 by chemical reaction. After $CO_2$ is removed in the $CO_2$ recovery section 18A, the $CO_2$-removed flue gas is brought into gas-liquid contact with circulating rinse water 21 including the $CO_2$ absorbent supplied from a liquid distributor in a rinsing section 18B in the $CO_2$ absorber 18 to recover the $CO_2$ absorbent 17 accompanying the $CO_2$-removed flue gas, and thereafter the flue gas 23 from which $CO_2$ has been removed is discharged outside the system. The pressure of the rich solution 19, which is the $CO_2$ absorbent in which $CO_2$ is absorbed, is raised by a rich solution pump 24 and the rich solution 19 is heated in a rich/lean solution heat exchanger 25 by the lean solution, which is the $CO_2$ absorbent 17 regenerated in the absorbent regenerator 20 and fed to the absorbent regenerator 20.

The rich solution 19 released from the top to the inside of the absorbent regenerator 20 is subjected to an endothermic reaction with the water vapor supplied from the bottom to release a large part of the $CO_2$. The $CO_2$ absorbent from which a part of or a large part of $CO_2$ has been released in the absorbent regenerator 20 is referred to as a semi-lean solution. When this semi-lean solution reaches the bottom of the absorbent regenerator 20, the semi-lean solution turns into a $CO_2$ absorbent 17 from which almost all $CO_2$ has been removed (lean solution). A part of this lean solution 17 is heated by steam 27 in a reboiler 26 to supply steam for $CO_2$ release inside the absorbent regenerator 20.

On the other hand, from the top part of the absorbent regenerator 20, $CO_2$-accompanying gas 28 with water vapor released from the rich solution 19 and the semi-lean solution in the regenerator is led out, the water vapor is condensed by a condenser 29, water is separated in a separation drum 30, and $CO_2$ gas 40 is released outside the system, separately compressed by a compressor 41, and recovered. This compressed and recovered $CO_2$ gas 42 passes through a separation drum 43 and thereafter is injected into an oil field using Enhanced Oil Recovery (EOR) or stored in an aquifer to take measures against global warming. Reflux water 31, which is separated and refluxed from the $CO_2$-accompanying gas 28 with steam in the separation drum 30, is supplied to each of the upper part of the absorbent regenerator 20 and the rinse water 21 side by a reflux water circulation pump 35. The regenerated $CO_2$ absorbent (lean solution) 17 is cooled by the rich solution 19 in the rich/lean solution heat exchanger 25, and subsequently the pressure of the regenerated $CO_2$ absorbent 17 is raised by a lean solution pump 32, cooled by a lean solution cooler 33, and thereafter fed into the $CO_2$ absorber 18. This embodiment only describes a general overview of the $CO_2$ recovery unit and some of the accompanying units are omitted from the description.

Hereinafter, suitable Examples that demonstrate the effects of the present disclosure will be described. The present disclosure, however, is not limited thereto.

Example

Figure 2:
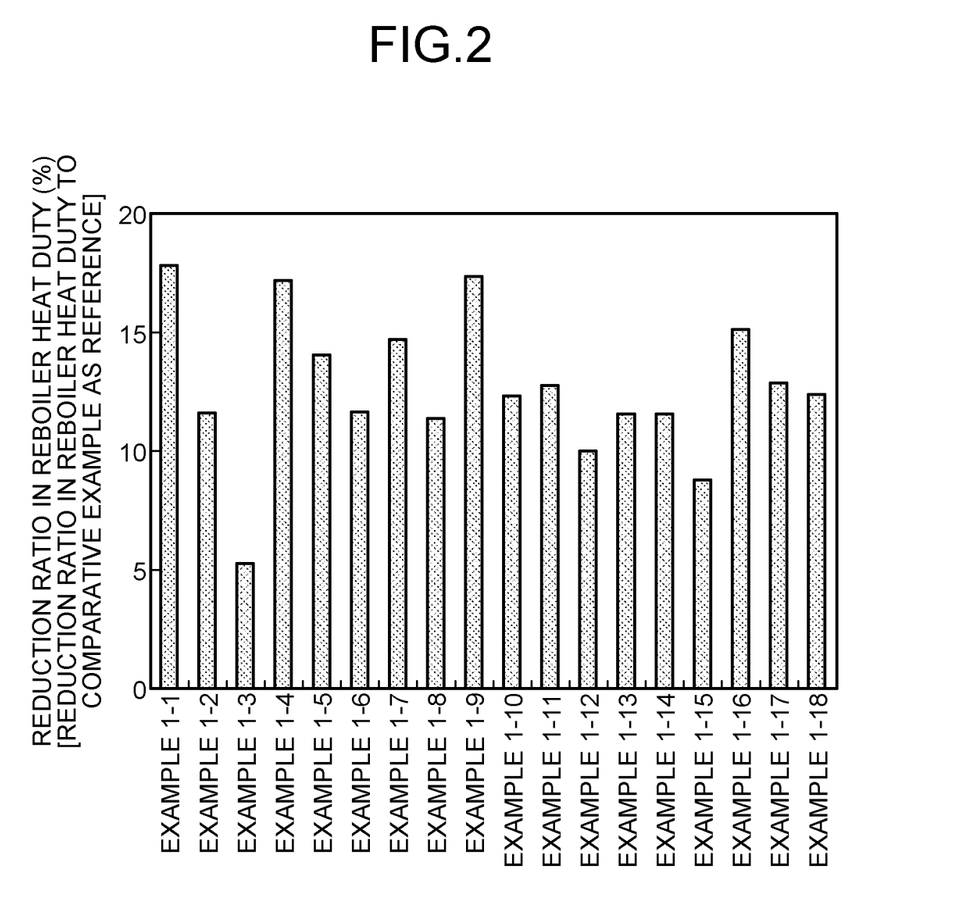
FIG. 2 is a graph illustrating each result of the reduction ratio in reboiler duty in Examples in Table 2 and first Comparative Example.

Absorption of $CO_2$ was performed using an absorption test apparatus, which is not illustrated. FIG. 2 is a graph illustrating the measured results of the relationship of the reduction ratio in reboiler duty between the three-component composite amine absorbent (a mixture formed by dissolving a linear chain monoamine (Component a), a diamine (Component b), and a cyclic compound (Component c) satisfying a chemical formula in water (Component d)) in Examples 1-1 to 1-18 and Comparative Example. The combinations of $R^1$ and $R^2$ of the cyclic compounds satisfying the chemical formula are listed in [Table 1] below and the list of components in the Examples is listed in [Table 2] below. In Examples below, the concentration of (linear chain monoamine (Component a)+diamine (Component b)) relative to the entire amount was determined to be 47% by weight to 60% by weight.

TABLE 1

| Chemical Formula | $R^1$ | $R^2$ |
|---|---|---|
| I-1 | H | O |
| I-2 | $CH_3$ | |
| I-3 | $CH_3-CH_2$ | |
| I-4 | $CH_3-CH_2-CH_2$ | |
| I-5 | $CH_3-CH_2-CH_2-CH_2$ | |
| I-6 | $HO-CH_2-CH_2$ | |
| I-7 | H | $N-CH_2-CH_2-OH$ |
| I-8 | $CH_3$ | |
| I-9 | $CH_3-CH_2$ | |
| I-10 | $CH_3-CH_2-CH_2$ | |
| I-11 | $CH_3-CH_2-CH_2-CH_2$ | |
| I-12 | $HO-CH_2-CH_2$ | |

In Example 1-2, the same amine components as the amine components in Example 1-1 were used and the concentration of Component c relative to the entire amount was determined to be 15% by weight. In Example 1-3, the same amine components as the amine components in Example 1-1 were used and the concentration of Component c relative to the entire amount was determined to be 5% by weight.

Subsequently, in Examples 1-4 to 1-18, the amine components were changed with respect to Example 1-1 and the concentration of Component c relative to the entire amount was determined to be between 15% by weight or more and 30% by weight or less. In the case where Component c is cyclic compounds satisfying a plurality of chemical formulas, the concentration of Component c relative to the entire amount is the total concentration of Component c.

In Example 1-4, an absorbent having the same composition as the composition in Example 1-1 was prepared except that the diamine (b) (Component b) was changed to propanediamine with respect to Example 1-1.

In Example 1-5, an absorbent having the same composition as the composition in Example 1-1 was prepared except that two cyclic compounds of a cyclic compound in which a combination of $R^1$ and $R^2$ was determined to be the chemical formula I-7 in Table 1 and a cyclic compound in which a combination of $R^1$ and $R^2$ was determined to be the chemical formula I-12 were used as the cyclic compounds (c) (Component c) satisfying the chemical formula.

TABLE 2

| | | | Cyclic compound (c) in Table 1.1 represented by Chemical Formula I | | Total concentration of (c) |
|---|---|---|---|---|---|
| Example | Chain monoamine (a) | Diamine (b) | Component | | (% by weight) |
| 1-1 | Monoethanolamine | 2-Amino-2-methyl-1-propanol | Piperazine | I-6 | — | 30 |
| 1-2 | Monoethanolamine | 2-Amino-2-methyl-1-propanol | Piperazine | I-6 | — | 15 |
| 1-3 | Monoethanolamine | 2-Amino-2-methyl-1-propanol | Piperazine | I-6 | — | 5 |
| 1-4 | Monoethanolamine | 2-Amino-2-methyl-1-propanol | Propanediamine | I-6 | — | 15-30 |
| 1-5 | Monoethanolamine | 2-Amino-2-methyl-1-propanol | Piperazine | I-7 | I-12 | |
| 1-6 | N-Ethylaminoethanol | — | 2-Methylpiperazine | I-9 | I-1 | |
| 1-7 | N-Ethylaminoethanol | — | Piperazine | I-3 | I-9 | |
| 1-8 | N-Butylaminoethanol | — | 2-Methylpiperazine | I-11 | I-1 | |
| 1-9 | N-Butylaminoethanol | — | Piperazine | I-5 | I-11 | |
| 1-10 | N-Ethylaminoethanol | 2-Amino-2-methyl-1-propanol | Piperazine | I-9 | I-1 | |
| 1-11 | N-Butylaminoethanol | 2-Amino-2-methyl-1-propanol | Piperazine | I-11 | I-1 | |
| 1-12 | N-Methyldiethanolamine | 2-Amino-2-methyl-1-propanol | Piperazine | I-8 | — | |
| 1-13 | N-Methyldiethanolamine | N-Ethylaminoethanol | Piperazine | I-8 | I-9 | |
| 1-14 | N-Methyldiethanolamine | N-Butylaminoethanol | Piperazine | I-8 | I-11 | |
| 1-15 | N-Ethyldiethanolamine | 2-Amino-2-methyl-1-propanol | Piperazine | I-9 | — | |
| 1-16 | N-Ethyldiethanolamine | N-Ethylaminoethanol | Piperazine | I-3 | I-9 | |
| 1-17 | N-Ethyldiethanolamine | N-Butylaminoethanol | Piperazine | I-9 | I-5 | |
| 1-18 | 4-Dimethylamino-1-butanol | 2-Amino-2-methyl-1-propanol | Piperazine | I-2 | — | |

Examples 1-1 to 1-3

In Example 1-1, monoethanolamine and 2-amino-2-methyl-1-propanol were used as the linear chain monoamines (a) (Component a), piperazine was used as the diamine (b) (Component b), and cyclic compounds in which a combination of $R^1$ and $R^2$ was determined to be the chemical formula I-6 in Table 1 were used as the cyclic compound (Component c) (c) satisfying the chemical formula, and these compounds were dissolved and mixed in water (Component d) to prepare absorbents. In Example 1-1, the concentration of Component c to the entire amount was determined to be 30% by weight.

In Examples 1-6, N-ethylaminoethanol was used as the linear chain monoamine (a) (Component a), 2-methylpiperazine was used as the diamine (b) (Component b), and two cyclic compounds of a cyclic compound in which a combination of $R^1$ and $R^2$ was determined to be the chemical formula I-9 in Table 1 and a cyclic compound in which a combination of $R^1$ and $R^2$ was determined to be the chemical formula I-1 were used as the cyclic compounds (c) (Component c) satisfying the chemical formula.

In Example 1-7, an absorbent having the same composition as the composition in Example 1-6 was prepared except that piperazine was used as the diamine (b) (Component b), and two cyclic compounds of a cyclic compound in which a combination of $R^1$ and $R^2$ was determined to be the chemical formula I-3 in Table 1 and a cyclic compound in which a combination of $R^1$ and $R^2$ was determined to be the chemical formula I-9 were used as the cyclic compounds (c) (Component c) satisfying the chemical formula.

In Examples 1-8, an absorbent having the same composition as the composition in Example 1-6 was prepared except that N-butylaminoethanol was used as the linear chain monoamine (a) (Component a), and two cyclic compounds of a cyclic compound in which a combination of $R^1$ and $R^2$ was determined to be the chemical formula I-11 in Table 1 and a cyclic compound in which a combination of $R^1$ and $R^2$ was determined to be the chemical formula I-1 were used as the cyclic compounds (c) (Component c) satisfying the chemical formula.

In Examples 1-9, an absorbent having the same composition as the composition in Example 1-7 was prepared except that N-butylaminoethanol was used as the linear chain monoamine (a) (Component a), and two cyclic compounds of a cyclic compound in which a combination of $R^1$ and $R^2$ was determined to be the chemical formula I-5 in Table 1 and a cyclic compound in which a combination of $R^1$ and $R^2$ was determined to be the chemical formula I-11 were used as the cyclic compounds (c) (Component c) satisfying the chemical formula.

In Examples 1-10, N-ethylaminoethanol and 2-amino-2-methyl-1-propanol were used as the linear chain monoamines (a) (Component a), piperazine was used as the diamine (b) (Component b), and two cyclic compounds of a cyclic compound in which a combination of $R^1$ and $R^2$ was determined to be the chemical formula I-9 in Table 1 and a cyclic compound in which a combination of $R^1$ and $R^2$ was determined to be the chemical formula I-1 were used as the cyclic compounds (c) (Component c) satisfying the chemical formula.

In Examples 1-11, N-butylaminoethanol and 2-amino-2-methyl-1-propanol were used as the linear chain monoamines (a) (Component a), piperazine was used as the diamine (b) (Component b), and two cyclic compounds of a cyclic compound in which a combination of $R^1$ and $R^2$ was determined to be the chemical formula I-11 in Table 1 and a cyclic compound in which a combination of $R^1$ and $R^2$ was determined to be the chemical formula I-1 were used as the cyclic compounds (c) (Component c) satisfying the chemical formula.

In Examples 1-12, N-methyldiethanolamine and 2-amino-2-methyl-1-propanol were used as the linear chain monoamines (a) (Component a), piperazine was used as the diamine (b) (Component b), and a cyclic compound in which a combination of $R^1$ and $R^2$ was determined to be the chemical formula I-8 in Table 1 was used as the cyclic compound (c) (Component c) satisfying the chemical formula.

In Examples 1-13, N-methyldiethanolamine and N-ethylaminoethanol were used as the linear chain monoamines (a) (Component a), piperazine was used as the diamine (b) (Component b), and two cyclic compounds of a cyclic compound in which a combination of $R^1$ and $R^2$ was determined to be the chemical formula I-8 in Table 1 and a cyclic compound in which a combination of $R^1$ and $R^2$ was determined to be the chemical formula I-9 were used as the cyclic compounds (c) (Component c) satisfying the chemical formula.

In Examples 1-14, N-methyldiethanolamine and N-butylaminoethanol were used as the linear chain monoamines (a) (Component a), piperazine was used as the diamine (b) (Component b), and two cyclic compounds of a cyclic compound in which a combination of $R^1$ and $R^2$ was determined to be the chemical formula I-8 in Table 1 and a cyclic compound in which a combination of $R^1$ and $R^2$ was determined to be the chemical formula I-11 were used as the cyclic compounds (c) (Component c) satisfying the chemical formula.

In Examples 1-15, N-ethyldiethanolamine and 2-amino-2-methyl-1-propanol were used as the linear chain monoamines (a) (Component a), piperazine was used as the diamine (b) (Component b), and a cyclic compound in which a combination of $R^1$ and $R^2$ was determined to be the chemical formula I-9 in Table 1 was used as the cyclic compound (c) (Component c) satisfying the chemical formula.

In Examples 1-16, N-ethyldiethanolamine and N-ethylaminoethanol were used as the linear chain monoamines (a) (Component a), piperazine was used as the diamine (b) (Component b), and two cyclic compounds of a cyclic compound in which a combination of $R^1$ and $R^2$ was determined to be the chemical formula I-3 in Table 1 and a cyclic compound in which a combination of $R^1$ and $R^2$ was determined to be the chemical formula I-9 were used as the cyclic compounds (c) (Component c) satisfying the chemical formula.

In Examples 1-17, N-ethyldiethanolamine and N-butylaminoethanol were used as the linear chain monoamines (a) (Component a), piperazine was used as the diamine (b) (Component b), and two cyclic compounds of a cyclic compound in which a combination of $R^1$ and $R^2$ was determined to be the chemical formula I-9 in Table 1 and a cyclic compound in which a combination of $R^1$ and $R^2$ was determined to be the chemical formula I-5 were used as the cyclic compounds (c) (Component c) satisfying the chemical formula.

In Examples 1-18, 4-dimethylamino-1-butanol and 2-amino-2-methyl-1-propanol were used as the linear chain monoamines (a) (Component a), piperazine was used as the diamine (b) (Component b), and a cyclic compound in which a combination of $R^1$ and $R^2$ was determined to be the chemical formula I-2 in Table 1 was used as the cyclic compound (c) (Component c) satisfying the chemical formula.

For each of Examples described above, reboiler duty at the time of a process in which the absorbent released $CO_2$ was measured. In test conditions, absorption conditions were 40° C. and 10 kPa $CO_2$ and a regeneration condition was 120° C. The absorbent in which $CO_2$ was absorbed in an absorber was heated with a reboiler in a regenerator and the heat duty was determined from the amount of steam supplied to the reboiler when the same amount of $CO_2$ was released from the regenerator and the specific enthalpy of steam under each condition. As Comparative Examples, absorbents in which the cyclic compound (c) of the chemical formula was not included and the total concentration of the linear chain monoamine (a) and the diamine (b) are the same as the total concentration of each Example, that is, Component c was substituted with water were prepared and the reduction ratio in reboiler duty was calculated by the same way with respect to each Example. FIG. 2 illustrates the results of the reduction ratios in reboiler duty when the reboiler duty in Comparative Example was determined to be 100%, that is, ((Reboiler duty in Comparative Example—Reboiler duty in Example/Reboiler duty in Comparative Example)×100 [%] was calculated with respect to each Example.

As illustrated in FIG. 2, use of the absorbents in Examples allows the reboiler duty, which is the heat duty required for releasing the target gas from the absorbent, to be reduced by 5% or more compared to the absorbent that does not include the cyclic compound (c) of the chemical formula. No difference in the efficiency of $CO_2$ absorption of the absorbent was observed between Examples and Comparative Examples.

Subsequently, with respect to Examples 1-5', 1-13', and 1-14' in Table 3 below, which are the same as Examples 1-5, 1-13, and 1-14, the reduction ratios in reboiler duty were measured in the case where the cyclic compounds (Component c) were replaced with the cyclic compounds in Comparative Examples. In Examples 1-5', 1-13', and 1-14' below, the concentrations of (linear chain monoamine (Component a)+diamine (Component b)) relative to the entire amount were set to 47% by weight to 55% by weight.

TABLE 3

| Example | Chain monoamine (a) | Diamine (b) | Cyclic compound (c) in Table 1.1 represented by Chemical Formula I | | Total concentration of (c) (% by weight) |
|---|---|---|---|---|---|
| | | | Component | | |
| 1-5' | Monoethanolamine | 2-Amino-2-methyl-1-propanol | Piperazine | I-7 | I-12 | 15-20 |
| 1-13' | N-Methyldiethanolamine | N-Ethylaminoethanol | Piperazine | I-8 | I-9 | |
| 1-14' | N-Methyldiethanolamine | N-Butylaminoethanol | Piperazine | I-8 | I-11 | |

In Comparative Examples, absorbents in which 1-(2-aminoethyl)-imidazolidin-2-one represented in [Chemical Formula 8] below was included instead of the cyclic compound of Component (c) in the same concentration in Examples were prepared.

Figure 3:
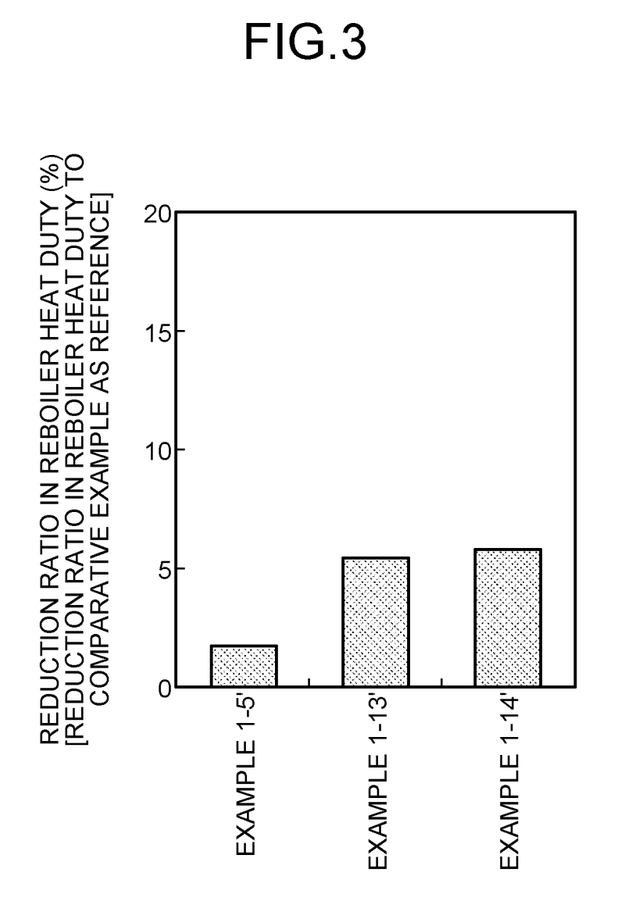
FIG. 3 is a graph illustrating each result of the reduction ratio in reboiler duty in Examples in Table 3 and first Comparative Example.

FIG. 3 illustrates the results of the reduction ratios in reboiler duty calculated based on the comparison between Examples and Comparative Examples. As illustrated in FIG. 3, use of the absorbents in Examples allows the reboiler duty, which is the heat duty required for releasing the target gas from the absorbent, to be reduced by 2% to 6% compared to an absorbent including the cyclic compound different from the present disclosure as Component (c).

Figure 4:
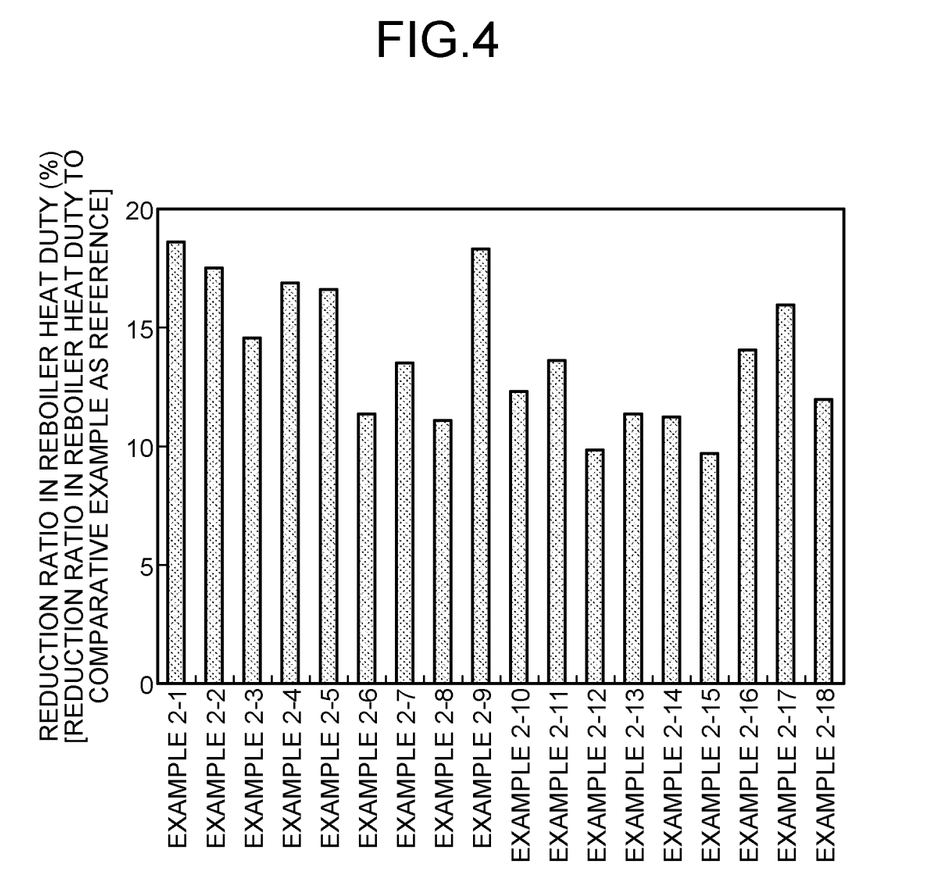
FIG. 4 is a graph illustrating each result of the reduction ratio in reboiler duty in Examples in Table 6 and second Comparative Example.

Subsequently, as Example 2, Example using an absorbent including a diamine (b1) containing amino groups having the same number of substituents and a chain diamine (b2) containing amino groups having the different numbers of substituents as the diamines of (Component b) will be described. FIG. 4 is a graph illustrating the results of measuring the relationship of the reduction ratios in reboiler duty between three-component composite amine absorbents (mixtures formed by dissolving the linear chain monoamine (Component a), the diamine containing amino groups having the same number of substituents (Component b1), the chain diamine containing amino groups having the different numbers of substituents (Component b2, and the cyclic compound (Component c) represented by the chemical formula illustrated in [Chemical Formula 2]) in water (Component d)) in Examples 2-1 to 2-18 and Comparative Examples. The combinations of $R^1$ and $R^2$ of cyclic compounds of (Component c) satisfying the chemical formula of [Chemical Formula 2] are listed in Table 4 below, the combinations of $R^4$, $R^5$, and $R^6$ in [Chemical Formula 6] of the chain diamines (Component b2) containing amino groups having the different numbers of substituents are listed in Table 5 below, and the list of components in Examples are listed in Table 6 below. In Examples below, the concentration of (linear chain monoamine (Component a)+diamine (Component b)) relative to the entire amount was determined to be 47% by weight to 60% by weight.

TABLE 4

| Chemical Formula | $R^1$ | $R^2$ |
|---|---|---|
| I-1 | H | O |
| I-2 | $CH_3$ | |
| I-3 | $CH_3-CH_2$ | |
| I-4 | $CH_3-CH_2-CH_2$ | |
| I-5 | $CH_3-CH_2-CH_2-CH_2$ | |
| I-6 | $HO-CH_2-CH_2$ | |
| I-7 | H | $N-CH_2-CH_2-OH$ |
| I-8 | $CH_3$ | |
| I-9 | $CH_3-CH_2$ | |
| I-10 | $CH_3-CH_2-CH_2$ | |
| I-11 | $CH_3-CH_2-CH_2-CH_2$ | |
| I-12 | $HO-CH_2-CH_2$ | |

TABLE 5

| Chemical Formula | $R^4$ | $R^5$ | $R^6$ |
|---|---|---|---|
| II-1 | H | H | $CH_2-CH_2-OH$ |
| II-2 | $CH_3$ | $CH_3$ | |
| II-3 | $CH_3-CH_2$ | $CH_2-CH_3$ | |
| II-4 | $CH_3-CH_2-CH_2$ | $CH_2-CH_2-CH_3$ | |
| II-5 | $CH_3-CH_2-CH_2-CH_2$ | $CH_2-CH_2-CH_2-CH_3$ | |
| II-6 | $HO-CH_2-CH_2$ | $CH_2-CH_2-OH$ | |

TABLE 5-continued

| Chemical Formula | $R^4$ | $R^5$ | $R^6$ |
|---|---|---|---|
| II-7 | $CH_3$ | $CH_2—CH_3$ | |
| II-8 | $CH_3—CH_2$ | $CH_3$ | |
| II-9 | $CH_3$ | $CH_2—CH_2—OH$ | |
| II-10 | $HO—CH_2—CH_2$ | $CH_3$ | |
| II-11 | $CH_3—CH_2$ | $CH_2—CH_2—OH$ | |
| II-12 | $HO—CH_2—CH_2$ | $CH_2—CH_3$ | |

TABLE 6

| Example | Chain monoamine (a) | Diamine (b1) containing amino groups having same number of substituents | Diamine (b2) containing amino groups having different number of substituents | Concentration of (b2) (% by weight) | Cyclic compound (c) in Table 1.1 represented by Chemical Formula I Component | Total concentration of (c) (% by weight) |
|---|---|---|---|---|---|---|
| 2-1 | Monoethanolamine | 2-Amino-2-methyl-1-propanol | Piperazine | II-1 | 13 | I-6 — | 20 |
| 2-2 | Monoethanolamine | 2-Amino-2-methyl-1-propanol | Piperazine | II-1 | 8 | I-6 — | 20 |
| 2-3 | Monoethanolamine | 2-Amino-2-methyl-1-propanol | Piperazine | II-1 | 1 | I-6 — | 20 |
| 2-4 | Monoethanolamine | 2-Amino-2-methyl-1-propanol | Propanediamine | II-1 | 3-8 | I-6 — | 10-20 |
| 2-5 | Monoethanolamine | 2-Amino-2-methyl-1-propanol | Piperazine | II-6 | | I-7 I-12 | |
| 2-6 | N-Ethylaminoethanol | — | 2-Methylpiperazine | II-11 | | I-9 I-1 | |
| 2-7 | N-Ethylaminoethanol | — | Piperazine | II-3 | | I-3 I-9 | |
| 2-8 | N-Butylaminoethanol | — | 2-Methylpiperazine | II-5 | | I-11 I-1 | |
| 2-9 | N-Butylaminoethanol | — | Piperazine | II-1 | | I-5 I-11 | |
| 2-10 | N-Ethylaminoethanol | 2-Amino-2-methyl-1-propanol | Piperazine | II-8 | | I-9 I-1 | |
| 2-11 | N-Butylaminoethanol | 2-Amino-2-methyl-1-propanol | Piperazine | II-1 | | I-11 I-1 | |
| 2-12 | N-Methyldiethanolamine | 2-Amino-2-methyl-1-propanol | Piperazine | II-9 | | I-8 — | |
| 2-13 | N-Methyldiethanolamine | N-Ethylaminoethanol | Piperazine | II-7 | | I-8 I-9 | |
| 2-14 | N-Methyldiethanolamine | N-Butylaminoethanol | Piperazine | II-10 | | I-8 I-11 | |
| 2-15 | N-Ethyldiethanolamine | 2-Amino-2-methyl-1-propanol | Piperazine | II-3 | | I-9 — | |
| 2-16 | N-Ethyldiethanolamine | N-Ethylaminoethanol | Piperazine | II-3 | | I-3 I-9 | |
| 2-17 | N-Ethyldiethanolamine | N-Butylaminoethanol | Piperazine | II-12 | | I-9 I-5 | |
| 2-18 | 4-Dimethylamino-1-butanol | 2-Amino-2-methyl-1-propanol | Piperazine | II-2 | | I-2 — | |

Examples 2-1 to 2-3

In Example 2-1, monoethanolamine and 2-amino-2-methyl-1-propanol were used as the linear chain monoamines (a) (Component a), piperazine was used as the diamine (b1) (Component b1) containing amino groups having the same number of substituents, a diamine in which a combination of $R^4$, $R^5$, and $R^6$ was determined to be the chemical formula II-1 in Table 5 was used as the chain amine (b2) (Component b2) containing amino groups having the different numbers of substituents, and a cyclic compound in which a combination of $R^1$ and $R^2$ was determined to be the chemical formula I-6 in Table 4 was used as the cyclic compound (c) (Component c) satisfying the chemical formula. In Example 2-1, the concentration of (Component b2) relative to the entire amount was set to 13% by weight and the concentration of (Component c) relative to the entire amount was set to 20% by weight.

In Example 2-2, the same amine components as the amine components in Example 2-1 were used and the concentration of (Component b2) relative to the entire amount was set to 8% by weight. In Example 2-3, the same amine components as the amine components in Example 2-1 were used and the concentration of (Component b2) relative to the entire amount was set to 1% by weight.

Subsequently, in Examples 2-4 to 2-18, the amine components were changed with respect to Example 2-1. The concentration of (Component b2) relative to the entire amount was set to 3% by weight to 8% by weight and the concentration of (Component c) relative to the entire amount was set to 10% by weight to 20% by weight.

In Example 2-4, an absorbent having the same compositions as the composition in Example 2-1 was prepared except that propanediamine was used as the diamine (b1) (Component b1) containing amino groups having the same number of substituents with respect to Example 2-1.

In Example 2-5, an absorbent having the same composition as the composition in Example 2-1 was prepared except that a diamine in which a combination of $R^4$, $R^5$, and $R^6$ was determined to be the chemical formula I-6 in Table 4 was used as the chain amine (b2) (Component b2) containing amino groups having the different numbers of substituents, and a cyclic compound in which a combination of $R^1$ and $R^2$ was determined to be the chemical formula I-7 in Table 4 and a cyclic compound in which a combination of $R^1$ and $R^2$ was determined to be the chemical formula I-12 in Table 4 were used as the cyclic compounds (c) (Component c) satisfying the chemical formula.

In Example 2-6, N-ethylaminoethanol was used as the linear chain monoamine (a) (Component a), 2-methylpiperazine was used as the diamine (b1) (Component b1) containing amino groups having the same number of substituents, a diamine in which a combination of $R^4$, $R^5$, and $R^6$ was determined to be the chemical formula II-11 in Table 5 was used as the chain amine (b2) (Component b2) containing amino groups having the different numbers of substituents, and a cyclic compound in which a combination of $R^1$ and $R^2$ was determined to be the chemical formula I-9 in Table 4 and a cyclic compound in which a combination of $R^1$ and $R^2$ was determined to be the chemical formula I-1 in Table 4 were used as the cyclic compounds (c) (Component c) satisfying the chemical formula.

In Example 2-7, N-ethylaminoethanol was used as the linear chain monoamine (a) (Component a), piperazine was used as the diamine (b1) (Component b1) containing amino groups having the same number of substituents, a diamine in which a combination of $R^4$, $R^5$, and $R^6$ was determined to be the chemical formula II-3 in Table 5 was used as the chain amine (b2) (Component b2) containing amino groups having the different numbers of substituents, and a cyclic compound in which a combination of $R^1$ and $R^2$ was determined to be the chemical formula I-3 in Table 4 and a cyclic compound in which a combination of $R^1$ and $R^2$ was determined to be the chemical formula I-9 in Table 4 were used as the cyclic compounds (c) (Component c) satisfying the chemical formula.

In Example 2-8, N-butylaminoethanol was used as the linear chain monoamine (a) (Component a), 2-methylpiperazine was used as the diamine (b1) (Component b1) containing amino groups having the same number of substituents, a diamine in which a combination of $R^4$, $R^5$, and $R^6$ was determined to be the chemical formula II-5 in Table 5 was used as the chain amine (b2) (Component b2) containing amino groups having the different numbers of substituents, and a cyclic compound in which a combination of $R^1$ and $R^2$ was determined to be the chemical formula I-11 in Table 4 and a cyclic compound in which a combination of $R^1$ and $R^2$ was determined to be the chemical formula I-1 in Table 4 were used as the cyclic compounds (c) (Component c) satisfying the chemical formula.

In Example 2-9, N-butylaminoethanol was used as the linear chain monoamine (a) (Component a), piperazine was used as the diamine (b1) (Component b1) containing amino groups having the same number of substituents, a diamine in which a combination of $R^4$, $R^5$, and $R^6$ was determined to be the chemical formula II-1 in Table 5 was used as the chain amine (b2) (Component b2) containing amino groups having the different numbers of substituents, and a cyclic compound in which a combination of $R^1$ and $R^2$ was determined to be the chemical formula I-5 in Table 4 and a cyclic compound in which a combination of $R^1$ and $R^2$ was determined to be the chemical formula I-11 in Table 4 were used as the cyclic compounds (c) (Component c) satisfying the chemical formula.

In Example 2-10, N-ethylaminoethanol and 2-amino-2-methyl-1-propanol were used as the linear chain monoamines (a) (Component a), piperazine was used as a diamine (b1) (Component b1) containing amino groups having the same number of substituents, a diamine in which a combination of $R^4$, $R^5$, and $R^6$ was determined to be the chemical formula II-8 in Table 5 was used as the chain amine (b2) (Component b2) containing amino groups having the different numbers of substituents, and a cyclic compound in which a combination of $R^1$ and $R^2$ was determined to be the chemical formula I-9 in Table 4 and a cyclic compound in which a combination of $R^1$ and $R^2$ was determined to be the chemical formula I-1 in Table 4 were used as the cyclic compounds (c) (Component c) satisfying the chemical formula.

In Example 2-11, N-butylaminoethanol and 2-amino-2-methyl-1-propanol were used as the linear chain monoamines (a) (Component a), piperazine was used as the diamine (b1) (Component b1) containing amino groups having the same number of substituents, a diamine in which a combination of $R^4$, $R^5$, and $R^6$ was determined to be the chemical formula II-1 in Table 5 was used as the chain amine (b2) (Component b2) containing amino groups having the different numbers of substituents, and a cyclic compound in which a combination of $R^1$ and $R^2$ was determined to be the chemical formula I-11 in Table 4 and a cyclic compound in which a combination of $R^1$ and $R^2$ was determined to be the chemical formula I-1 in Table 4 were used as the cyclic compounds (c) (Component c) satisfying the chemical formula.

In Example 2-12, N-methyldiethanolamine and 2-amino-2-methyl-1-propanol were used as the linear chain monoamines (a) (Component a), piperazine was used as a diamine (b1) (Component b1) containing amino groups having the same number of substituents, a diamine in which a combination of $R^4$, $R^5$, and $R^6$ was determined to be the chemical formula II-9 in Table 5 was used as the chain amine (b2) (Component b2) containing amino groups having the different numbers of substituents, and a cyclic compound in which a combination of $R^1$ and $R^2$ was determined to be the chemical formula I-8 in Table 4 was used as the cyclic compound (c) (Component c) satisfying the chemical formula.

In Example 2-13, N-methyldiethanolamine and N-ethylaminoethanol were used as the linear chain monoamines (a) (Component a), piperazine was used as the diamine (b1) (Component b1) containing amino groups having the same number of substituents, a diamine in which a combination of $R^4$, $R^5$, and $R^6$ was determined to be the chemical formula II-7 in Table 5 was used as the chain amine (b2) (Component b2) containing amino groups having the different numbers of substituents, and a cyclic compound in which a combination of $R^1$ and $R^2$ was determined to be the chemical formula I-8 in Table 4 and a cyclic compound in which a combination of $R^1$ and $R^2$ was determined to be the chemical formula I-9 in Table 4 were used as the cyclic compounds (c) (Component c) satisfying the chemical formula.

In Example 2-14, N-methyldiethanolamine and N-butylaminoethanol were used as the linear chain monoamines (a) (Component a), piperazine was used as the diamine (b1) (Component b1) containing amino groups having the same number of substituents, a diamine in which a combination of $R^4$, $R^5$, and $R^6$ was determined to be the chemical formula II-10 in Table 5 was used as the chain amine (b2) (Component b2) containing amino groups having the different numbers of substituents, and a cyclic compound in which a combination of $R^1$ and $R^2$ was determined to be the chemical formula I-8 in Table 4 and a cyclic compound in which a combination of $R^1$ and $R^2$ was determined to be the chemical formula I-11 in Table 4 were used as the cyclic compounds (c) (Component c) satisfying the chemical formula.

In Example 2-15, N-ethyldiethanolamine and 2-amino-2-methyl-1-propanol were used as the linear chain monoamines (a) (Component a), piperazine was used as the diamine (b1) (Component b1) containing amino groups having the same number of substituents, a diamine in which a combination of $R^4$, $R^5$, and $R^6$ was determined to be the chemical formula II-3 in Table 5 was used as the chain amine (b2) (Component b2) containing amino groups having the different numbers of substituents, and a cyclic compound in which a combination of $R^1$ and $R^2$ was determined to be the chemical formula I-9 in Table 4 was used as the cyclic compound (c) (Component c) satisfying the chemical formula.

In Example 2-16, N-ethyldiethanolamine and N-ethylaminoethanol were used as the linear chain monoamines (a)

(Component a), piperazine was used as the diamine (b1) (Component b1) containing amino groups having the same number of substituents, a diamine in which a combination of $R^4$, $R^5$, and $R^6$ was determined to be the chemical formula II-3 in Table 4 was used as the chain amine (b2) (Component b2) containing amino groups having the different numbers of substituents, and a cyclic compound in which a combination of $R^1$ and $R^2$ was determined to be the chemical formula I-3 in Table 4 and a cyclic compound in which a combination of $R^1$ and $R^2$ was determined to be the chemical formula I-9 in Table 4 were used as the cyclic compounds (c) (Component c) satisfying the chemical formula.

In Example 2-17, N-ethyldiethanolamine and N-butylaminoethanol were used as the linear chain monoamines (a) (Component a), piperazine was used as the diamine (b1) (Component b1) containing amino groups having the same number of substituents, a diamine in which a combination of $R^4$, $R^5$, and $R^6$ was determined to be the chemical formula II-12 in Table 5 was used as the chain amine (b2) (Component b2) containing amino groups having the different numbers of substituents, and a cyclic compound in which a combination of $R^1$ and $R^2$ was determined to be the chemical formula I-9 in Table 4 and a cyclic compound in which a combination of $R^1$ and $R^2$ was determined to be the chemical formula I-5 in Table 4 were used as the cyclic compounds (c) (Component c) satisfying the chemical formula.

In Example 2-18, 4-dimethylamino-1-butanol and 2-amino-2-methyl-1-propanol were used as the linear chain monoamines (a) (Component a), piperazine was used as the diamine (b1) (Component b1) containing amino groups having the same number of substituents, a diamine in which a combination of $R^4$, $R^5$, and $R^6$ was determined to be the chemical formula II-2 in Table 5 was used as the chain amine (b2) (Component b2) containing amino groups having the different numbers of substituents, and a cyclic compound in which a combination of $R^1$ and $R^2$ was determined to be the chemical formula I-2 in Table 4 was used as the cyclic compounds (c) (Component c) satisfying the chemical formula.

As Comparative Examples, an absorbent in which the chain diamine (b2) (Component b2) containing amino groups having the different numbers of substituents and the cyclic compound (c) satisfying the chemical formula (Component c) were not included in their weight and the weight of the linear chain monoamine (a) (Component a) and the diamine (b1) (Component b1) containing the amino groups having the same number of substituents was the same as in each Example was prepared as Comparative Example to calculate similar heat duty of the reboiler. FIG. 4 illustrates the results of calculating the reduction ratios in reboiler duty in Examples with respect to each Example when reboiler duty in Comparative Example is determined to be 1.

As illustrated in FIG. 4, use of the absorbents in Examples allows heat quantity of the reboiler to be reduced by 10% or more compared to the absorbents in Comparative Examples.

As described in above Examples, use of the composite amine absorbent including the chain monoamine (a), diamine (b), a cyclic compound (c) satisfying [Chemical Formula 2], and water (d) allows the release of absorbed $CO_2$ and $H_2S$ to be easily released and heat duty required for absorbed gas stripping to be reduced. This allows the energy required for $CO_2$ and $H_2S$ recovery to be further reduced. The reaction rate can also be maintained as the absorbent. This allows performance as the absorbent to be improved.

The present disclosure discloses the following inventions. The present disclosure is not limited to the following inventions.

(1) A composite amine absorbent to absorb at least one of $CO_2$ and $H_2S$ in a gas, the composite amine absorbent including:
a chain monoamine (a);
a diamine (b); and
a cyclic compound (c) represented by the following chemical formula:

where $R^2$: oxygen or $N$—$R^3$, and
$R^3$: any one of hydrogen, a hydrocarbon group, and a hydroxyalkyl group having a carbon number of 1 to 4; and
water (d).

(2) The composite amine absorbent as described in (1), wherein the chain monoamine (a) includes at least one of a primary chain monoalkanolamine, a secondary chain monoalkanolamine, and a tertiary chain monoalkanolamine.

(3) The composite amine absorbent as described in (1) or (2), wherein the diamine (b) includes at least one diamine containing amino groups having the same number of substituents.

(4) The composite amine absorbent as described in (3), wherein the diamine containing amino groups having the same number of substituents includes at least one of a primary chain polyamine, a secondary chain polyamine, and a secondary cyclic polyamine.

(5) The composite amine absorbent as described in (1) or (2), wherein the diamine (b) includes at least one diamine containing amino groups having the same number of substituents and at least one chain diamine containing amino groups having different numbers of substituents.

(6) The composite amine absorbent as described in (5), wherein the diamine containing amino groups having the same number of substituents includes at least one of a primary chain polyamine, a secondary chain polyamine, and a secondary cyclic polyamine.

(7) The composite amine absorbent as described in (5), wherein the chain diamine containing amino groups having the different numbers of substituents includes at least one compound satisfying:

$R^4$: any one of hydrogen, a hydrocarbon group having a carbon number of 1 to 4, and a hydroxyalkyl group,
$R^5$: any one of hydrogen, a hydrocarbon group having a carbon number of 1 to 4, and a hydroxyalkyl group, and
$R^6$: a hydroxyalkyl group, and
wherein for $R^4$ not being hydrogen, $R^5$ is also not hydrogen.

(8) The composite amine absorbent as described in any one of (1) to (7), wherein a total concentration of the chain monoamine (a), the diamine (b), and the cyclic compound (c) of the chemical formula is 20% by weight or more and 80% by weight or less relative to the entire absorbent.

(9) The composite amine absorbent as described in any one of (1) to (8), wherein a concentration of the chain monoamine (a) is 15% by weight or more and 60% by weight or less relative to the entire absorbent.

(10) The composite amine absorbent as described in any one of (1) to (9), wherein a concentration of the diamine (b) is 1% by weight or more and 25% by weight or less relative to the entire absorbent.

(11) The composite amine absorbent as described in (1) to (10), wherein a concentration of the cyclic compound (c) of the formula is 1% by weight or more and 30% by weight or less relative to the entire absorbent.

(12) The composite amine absorbent as described in any one of (1) to (11), wherein a weight ratio of ((diamine (b)+cyclic compound (c) of chemical formula/(chain monoamine (a))) is $0.033 \leq (b+c)/a \leq 3.7$.

(13) The composite amine absorbent as described in any one of (1) to (12), wherein a weight ratio of diamine (b)/cyclic compound (c) of chemical formula is a blend of $0.033 \leq b/c \leq 18$.

(14) A removal unit using the composite amine absorbent as described in any one of (1) to (13), the removal unit including:
an absorber configured to bring a gas including at least one of $CO_2$ and $H_2S$ into contact with the absorbent to remove at least one of $CO_2$ and $H_2S$; and
an absorbent regenerator configured to regenerate a solution absorbing at least one of $CO_2$ and $H_2S$,
wherein the regenerated solution formed by removing at least one of $CO_2$ and $H_2S$ in the absorbent regenerator is reused in the absorber.

(15) The removal unit as described in (14), wherein
the absorber has an absorbing temperature of 30° C. to 80° C., and
the absorbent regenerator has a regeneration temperature of 110° C. or more.

(16) A removal method using the composite amine absorbent as described in any one of (1) to (13), the removal method including:
bringing a gas including at least one of $CO_2$ and $H_2S$ into contact with the absorbent to remove at least one of $CO_2$ and $H_2S$ in an absorber;
regenerating a solution absorbing at least one of $CO_2$ and $H_2S$ in an absorber regenerator; and
reusing in the absorber the solution regenerated by removing at least one of $CO_2$ and $H_2S$ in the absorbent regenerator.

(17) The removal method according to claim 16, wherein
an absorbing temperature in the absorber is 30° C. to 80° C.; and
a regeneration temperature in the absorbent regenerator is 110° C. or more.

REFERENCE SYMBOLS LIST

12 $CO_2$ Recovery Unit
13 Industrial Combustion Facility
14 Flue Gas
16 Flue Gas Cooling Device
17 $CO_2$ Absorbent (Lean Solution)
18 $CO_2$ Absorber
19 $CO_2$-Absorbed $CO_2$ Absorbent (Rich Solution)
20 Absorbent Regenerator
21 Rinse water

The invention claimed is:

1. A composite amine absorbent to absorb at least one of $CO_2$ and $H_2S$ in a gas, the composite amine absorbent comprising:
a chain monoamine (a);
a diamine (b);
a cyclic compound (c) represented by following chemical formula:

where $R^1$: either hydrogen or a hydrocarbon group having a carbon number of 1 to 4,
$R^2$: oxygen or $N-R^3$, and
$R^3$: any one of hydrogen and a hydroxyalkyl group; and
water (d),
wherein
the diamine (b) comprises at least one diamine containing amino groups having a same number of substituents,
a concentration of the chain monoamine (a) is 15% by weight or more and 60% by weight or less relative to the entire absorbent,
a concentration of the diamine (b) is 1% by weight or more and 25% by weight or less relative to the entire absorbent, and
a concentration of the cyclic compound (c) of the formula is 1% by weight or more and 30% by weight or less relative to the entire absorbent.

2. The composite amine absorbent according to claim 1, wherein the chain monoamine (a) comprises at least one of a primary chain monoalkanolamine, a secondary chain monoalkanolamine, and a tertiary chain monoalkanolamine.

3. The composite amine absorbent according to claim 1, wherein the diamine containing amino groups having the same number of substituents comprises at least one of a primary chain polyamine, a secondary chain polyamine, and a secondary cyclic polyamine.

4. The composite amine absorbent according to claim 1, wherein the diamine (b) comprises at least one diamine containing amino groups having a same number of substituents and at least one chain diamine containing amino groups having different numbers of substituents.

5. The composite amine absorbent according to claim 4, wherein the diamine containing amino groups having the same number of substituents comprises at least one of a primary chain polyamine, a secondary chain polyamine, and a secondary cyclic polyamine.

6. The composite amine absorbent according to claim 4, wherein the chain diamine containing amino groups having the different numbers of substituents comprises at least one compound satisfying:

where $R^4$: any one of hydrogen, a hydrocarbon group having a carbon number of 1 to 4, and a hydroxyalkyl group, R⁵: any one of hydrogen, a hydrocarbon group having a carbon number of 1 to 4, and a hydroxyalkyl group, and R⁶: a hydroxyalkyl group, and wherein for $R^4$ not being hydrogen, $R^5$ is also not hydrogen.

7. The composite amine absorbent according to claim 1, wherein a total concentration of the chain monoamine (a), the diamine (b), and the cyclic compound (c) of the chemical formula is 20% by weight or more and 80% by weight or less relative to the entire absorbent.

8. The composite amine absorbent according to claim 1, wherein a weight ratio of ((diamine (b)+cyclic compound (c) of chemical formula)/(chain monoamine (a))) is 0.033≤(b+c)/a≤3.65.

9. The composite amine absorbent according to claim 1, wherein a weight ratio of diamine (b)/cyclic compound (c) of chemical formula is a blend of 0.033≤b/c≤18.

10. A removal unit using the composite amine absorbent according to claim 1, the removal unit comprising:
    an absorber configured to bring a gas including at least one of CO2 and H2S into contact with the absorbent to remove at least one of CO2 and H2S; and
    an absorbent regenerator configured to regenerate a solution absorbing at least one of CO2 and H2S,
    wherein the regenerated solution formed by removing at least one of CO2 and H2S in the absorbent regenerator is reused in the absorber.

11. The removal unit according to claim 10, wherein
    the absorber has an absorbing temperature of 30° C. to 80° C., and
    the absorbent regenerator has a regeneration temperature of 110° C. or more.

12. A removal method using the composite amine absorbent according to claim 1, the removal method comprising:
    bringing a gas including at least one of $CO_2$ and $H_2S$ into contact with the absorbent to remove at least one of $CO_2$ and $H_2S$ in an absorber;
    regenerating a solution absorbing at least one of $CO_2$ and $H_2S$ in an absorber regenerator; and
    reusing in the absorber the solution regenerated by removing at least one of CO2 and H2S in the absorbent regenerator.

13. The removal method according to claim 12, wherein
    an absorbing temperature in the absorber is 30° C. to 80° C.; and
    a regeneration temperature in the absorbent regenerator is 110° C. or more.

* * * * *